United States Patent [19]

Streit et al.

[11] 4,178,264

[45] Dec. 11, 1979

[54] AIR TREATING GEL COMPOSITION

[75] Inventors: Allan L. Streit, Hackensack, N.J.; Edward Sansanelli, Rio De Janiero, Brazil

[73] Assignee: Airwick Industries, Inc., Carlstadt, N.J.

[21] Appl. No.: 873,827

[22] Filed: Jan. 31, 1978

[51] Int. Cl.² .................... B01J 13/00; A61K 7/46; A61L 13/04
[52] U.S. Cl. .................... 252/316; 252/522; 422/5; 424/76
[58] Field of Search .................... 252/316, 522; 424/76; 21/55; 422/5

[56] References Cited

U.S. PATENT DOCUMENTS

| | | | |
|---|---|---|---|
| 2,691,615 | 10/1954 | Turner et al. | 424/76 X |
| 2,871,526 | 2/1959 | Bulloff | 21/55 X |
| 2,927,055 | 3/1960 | Lanzet | 424/76 |
| 3,767,787 | 10/1973 | Segal | 424/76 |
| 4,056,612 | 11/1977 | Lin | 424/76 |

FOREIGN PATENT DOCUMENTS

| | | | |
|---|---|---|---|
| 2123824 | 9/1972 | France | 424/76 |
| 1241914 | 8/1971 | United Kingdom | 424/76 |

*Primary Examiner*—Richard D. Lovering
*Attorney, Agent, or Firm*—Frederick H. Rabin

[57] ABSTRACT

An improved air treating gel of significantly enhanced stability, primarily thermal stability, comprising in an aqueous system a weight ratio of from about 0.3:1 to 5:1 carrageenan to stearate salt; a volatile active agent; a stearate solubility enhancer; and water.

7 Claims, No Drawings

AIR TREATING GEL COMPOSITION

The general type of air treating gel with which the present invention is concerned has been disclosed in U.S. Pat. Nos. 2,691,615 and 2,927,055. Such air treating gels are there described and claimed as consisting of an aqueous medium containing a plurality of volatile air treating components which are compatible, uniformly dispersible in water, and which normally volatilize at different rates at room temperature, and an aqueous gelling agent, the amount of gelling agent present in proportion to the aqueous medium being such that the gel is firm and substantially devoid of syneresis. It is also pointed out in said patents that a distinct advantage in the air treating gel over the previously known air treating compositions in liquid form is that the slow diffusion of liquid composition to the surface thereof for evaporation so retards and controls the evaporation that vapors of substantially uniform quality or composition are emitted during the useful life of the gel, i.e. during the period from initial exposure to air to the time when the aqueous medium containing volatile components has been substantially dissipated from the get. The use of such gels for introducing mixtures of volatile air treating materials into air has been particularly advantageous in the field of air freshening and deodorization when treating air in rooms or other confined spaces.

During recent years, a number of solid air treating compositions have been marketed with a reasonable degree of success. These compositions, which are primarily based on carrageenan, release perfume or odor counteractants continuously over a period of time. Although carrageenan adequately forms gels and is capable of entrapping essential oils and aromatics for slow release, the physical properties of the carrageenan gel create a number of problems which must be closely watched during production and formulation. One of the most important problems regarding carrageenan is a problem known as syneresis, i.e. the loss of moisture from the gel to the surface which gives the gel a wet appearance and can create difficulties. The syneresis problem can be alleviated in carrageenan gels by using sufficiently high percentages of the carrageenan gelling agent. However, carrageenan is an expensive material and it is very difficult to produce an economical solid air treating gel without having significant amounts of syneresis.

A major disadvantage of such carrageenan systems is their lack of stability when such gels are exposed to the extreme temperatures frequently encountered during storage and/or shipping in the summer and winter months. Such lack of stability is exhibited by one or more of the following: product weight loss, deterioration of the product appearance, loss of effectivenes, and the like. Specifically, such carrageenan-based compositions show poor freeze-thaw stability in that samples which return to ambient temperatures from temperatures below about $-20°$ C. exhibit a significant fluid loss and corresponding reduction in size and appearance.

Other gel compositions are prepared utilizing stearate salt gelling agents. Although stearates also adequately form gels and entrap volatiles they too exhibit poor temperature stability, in this instance at high temperatures. Thus, samples which are returned to ambient temperatures after having been exposed to temperatures above about 48° C. lose their integrity completely and return to their liquid state. It should be recognized that this difficulty is a meaningful one in that such temperatures can be reached in warehouses and the like during hot summer months or in tropical climates.

It is, therefore, the primary object of this invention to provide an air treating gel composition of significantly improved thermal stability.

It is a further object to provide such a gel composition without adversely effecting the other essential properties thereof.

It is a still further object to provide a gel composition which is simple and economical to produce.

Various other objects and advantages of this invention will become apparent from the following description thereof.

It has now been discovered that an air treating gel having both high and low temperature stability as well as superior appearance and quality can be prepared utilizing as gelling agent a novel blend of carrageenan and stearate salt. Thus, such compositions substantially eliminate the weight loss and reduction in efficacy and appearance experienced by carrageenan gels at low temperatures and the loss of integrity experienced by stearate gels at elevated temperatures. They can be simply and economically prepared. They are rigid yet sufficiently flexible to resist crumbling. These gels are sufficiently strong and provide a uniform release of the active ingredients.

The air treating gels of the present invention comprise from about 1.5–15%, by weight, of a 0.3:1 to 5:1 weight ratio of carrageenan and stearate salt; from about 0.5–6.0%, by weight, of essential oils and aromatics; from about 1.0 to 20.0%, by weight, of a solvent component; with the balance being water.

As noted, the carrageenan and the sterate salt are present as the gel ingredient in the weight reatio of 0.3:1 to 5:1, and preferably 1:1 to 3:1, in order to provide the substantially improved thermal stability described herein. Concentrations which reflect additional amounts of either ingredient beyond the indicated range result in gels which tend to exhibit the disadvantages noted with gels prepared from the individual gelling agents.

Applicable stearates include sodium and potassium stearates as well as alkanolamine stearates such as triethanolamine, diethanolamine, triisopropanolamine and monoisopropanolamine stearates.

The solvent component is present for the purpose of enhancing the solubility of the stearate component, improving the total emulsion, controlling the rate of evaporation and generally contributing to an improvement of freeze-thaw stability. Among applicable solvents are included glycols such as ethylene glycol, diethylene glycol, triethylene glycol and tetraethylene glycol and propylene glycol; liquid polyethylene glycols ranging in average molecular weight from about 200 to 600; solid polyethylene glycols ranging in average molecular weight from about 1000 to 7500; ethylene and polyethylene glycol monomethyl ethers such as 2-methoxy-ethanol, 2-(2-methoxyethoxy) ethanol, 1-methyl-2-methoxyethanol and 1-methyl-2-(1-methyl-2-methoxyethoxy) ethanol; and mixtures thereof; and $C_2$–$C_{18}$ alcohols such as ethanol, butanol, hexanol and cetyl alcohol. Polyethylene glycols are commercially sold by Union Carbide Corporation under the trademark designation of CARBOWAX. The glycol ethers are also commercially sold by Union Carbide Corporation under the trademark designations CELLO- SOLVE, CARBITOL and UCAR. The preferred solvents are propylene glycol, ethylene glycol and ethanol.

The primary volatile agents are all conventional fragrances, i.e. volatile odorous agents, including essential oils, aromatic chemicals and the like, applicable for use in the instant formulations. A wide variety of such materials is known to those skilled in the perfuming arts. they may comprise one or more natural materials or synthetic aromatic agents or mixtures of the two.

The gels of the present invention are aqueous gels and water comprises from 55 to 95% and preferably from 80 to 90% of the total composition. It is suitable to use ordinary tap water since the small percentage of ions normally present do not adversely effect the gels of the present invention. Of course, deionized or distilled water could be used if desired.

The air freshener gel may contain small amounts of various optional ingredients. Such optional ingredients may include up to about 3.0% silicone emulsion, up to about 3% nonionic emulsifiers, up to about 1% preservative and up to about 1% pigment dispersions or water soluble dyes, as well as bacteriostats and the like. Care should be exercised in selecting the amount of optional ingredients so as to avoid adversely effecting gel performance.

In preparing air treating gels in accordance with the present invention, the carrageenan is initially slowly added to water maintained at a temperature of from about 45° to 70° C. The solution is heated to a temperature of from about 80° to 95° C. for complete hydration of the powder and then cooled to a temperature of from about 65° to 90° C. Thereafter, either (a) the glycol and stearate are individually dispersed in the carrageenan solution; or (b) the solvent is heated to above 85° C. in a separate vessel in which the stearate is dispersed and the hot solution is added, under agitation, to the carrageenan solution. Finally, a clear, pre-mixed solution of active agent and any optional emulsifiers are added to the hot gel solution whereupon the gel is cooled to about 60° to 85° C., poured into a mold and allowed to cool to produce the formed gel masses.

The compositions of the present invention are sufficiently rigid so as to be generally free-standing yet are sufficiently flexible to resist crumbling or breaking. These materials do not require a central core of other material to support the same, but can be poured directly into a container which can be maintained in an upright condition. The gels generally have sufficient strength so that they will not sag but will be maintained in the container so that air can easily and freely contact the surface of the same to transfer the perfume to the surrounding room. If it is desirable, however, to form the air treating gel in a tub or other container without regard to the rigidity, the amounts of material can be reduced significantly to form a gel which will be sufficiently rigid so as not to flow out of the container if tilted, yet cannot be said to be sufficiently self-supporting to enable the same to be packed in a relatively cylindrical or upright container. Of primary importance, the compositions form a synergistic gel system which exhibits minimal (less than about 1%) syneresis and which maintains its integrity when exposed to temperatures ranging from about −25° C. to 58° C.

The gelling formulation may be utilized in the preparation of many types of air treating gels adapted for the introduction of mixtures of active volatile components into air. Thus, while of particular importance in the preparation of gels for air freshening and odor counteraction, the improved gelling agent can be used in the preparation of gels having insect repellent, insecticidal, bronchodilatory and decongestant properties as well as gels for the emission of controlled scents or perfumes, and the like.

The following examples will further illustrate the embodiment of this invention. In these exampes, all parts given are by weight unless otherwise noted.

Example I

This example illustrates the preparation of a typical gel composition of the instant invention as well as the substantially improved freeze-thaw stability thereof.

The following formulations were prepared by adding the carrageenan to water at 49° C., heating the solution to 82° C., and cooling to 71° C. Thereafter, the glycol, stearate and perfume were individually dispersed in the hot carrageenan solution. The resulting gel composition was then cooled.

|  | parts | | | | |
| --- | --- | --- | --- | --- | --- |
|  | 1 | 2 | 3 | 4 | 5 |
| Carrageenan | 5.1 | — | — | 3.1 | 3.1 |
| Sodium Stearate | — | 5.1 | — | 2.0 | — |
| Potassium Stearate | — | — | 5.1 | — | 2.0 |
| Propylene Glycol | 6.0 | 6.0 | 6.0 | 6.0 | 6.0 |
| Perfume | 3.0 | 3.0 | 3.0 | 3.0 | 3.0 |
| Tap Water | balance to 100 | | | | |
| Physical State @ RT | solid | solid | liquid | solid | solid |
| Physical State @ 54° C. | solid | liquid | — | solid | solid |

Formulations 1,2,4 and 5 were then subjected to the following freeze-thaw test procedure. A pre-weighed gel unit was placed in a freezer at a temperature of −18° C. The gel was removed when it reached −18° C. (18 hours). The gel unit was then thawed under ambient conditions until it stabilized at room temperature (8 hours). All excessive syneresis was removed and the unit reweighed to determine % weight loss. The following weight loss values were obtained:

|  | % weight loss |
| --- | --- |
| 1 | 2.4 |
| 2 | 1.8 |
| 4 | 0.2 |
| 5 | 1.0 |

The results thus indicate the excellent physical characteristics of the novel gels of this invention as well as the synergistic properties derived from utilizing the carrageenan-stearate blend as the primary gelling agent.

Example II

The following formulations were prepared utilizing the procedure of Example I. In this instance, the glycol, stearate, silicone emulsion and pigment dispersion were individually added to the hot carrageenan and, thereafter, a pre-mixed blend of perfume, emulsifier ad preservative was added.

|  | parts | | |
| --- | --- | --- | --- |
|  | 6 | 7 | 8 |
| Carageenan-(Kappa fraction) | 2.40 | — | 2.40 |
| Carageenan-(Iota fraction) | 0.60 | — | 0.60 |
| Tap Water | 93.22 | 70.22 | 82.68 |
| Pigment Dispersion | 0.03 | 0.03 | 0.03 |
| Fragrance Oils | 2.50 | 2.50 | 2.50 |

-continued

|  | parts | | |
| --- | --- | --- | --- |
|  | 6 | 7 | 8 |
| Nonionic Surfactant | 1.00 | — | 1.00 |
| Bacteriostat | 0.25 | 0.25 | 0.25 |
| Propylene Glycol | — | 15.00 | 6.40 |
| Polymer Emulsion | — | 2.50 | 1.07 |
| Ethyl Alcohol | — | 2.50 | 1.07 |
| Sodium Stearate | — | 7.00 | 2.00 |

In addition, the respective formulations were subjected to the freeze-thaw test of Example I and a heat stability test which involved heating the gel unit to 54° C., cooling it to room temperature and determining % syneresis.

| Formulation | % Syneresis (−18° C. - Ambient) | % Syneresis (54° C. - Ambient) |
| --- | --- | --- |
| 6** | 5.97 | 0.59 |
|  | 24.48 | 0.39 |
|  | 11.73 | 0.47 |
| 7** | 0.01 | * |
|  | 0.03 | * |
|  | 0.02 | * |
| 8** | 0.13 | 0.17 |
|  | 0.03 | 0.22 |
|  | 0.25 | 0.18 |

*Integrity lost and returned to liquid state.
**Three independently prepared samples.

Example III

The following formulations were prepared by the method of Example II.

|  | parts | | | | | |
| --- | --- | --- | --- | --- | --- | --- |
|  | 9 | 10 | 11 | 12 | 13 | 14* |
| Carrageenan | 3.00 | — | 2.00 | 7.50 | — | 4.95 |
| Tap Water | 89.75 | 89.75 | 89.75 | 82.25 | 82.25 | 82.25 |
| Pigment Dispersion | 0.30 | —.30 | 0.30 | 0.30 | 0.30 | 0.30 |
| Fragrance Oils | 3.00 | 3.00 | 3.00 | 3.00 | 3.00 | 3.00 |
| Nonionic Surfactant | 0.60 | 0.60 | 0.60 | 0.60 | 0.60 | 0.60 |
| Bacteriostat | 0.25 | 0.25 | 0.25 | 0.25 | 0.25 | 0.25 |
| Propylene Glycol | 3.00 | 3.00 | 3.00 | 6.00 | 6.00 | 6.00 |
| Sodium Stearate | — | 3.00 | 1.00 | — | 7.50 | 2.55 |
| Silicone Emulsion | 0.10 | 0.10 | 0.10 | 0.10 | 0.10 | 0.10 |
| Physical State @ R.T. | Solid | Liquid | Solid | ** | Solid | Solid |
| Physical State @ 54° C. | Solid | — | Solid | ** | Liquid | Solid |
| % Weight Loss @ 18° C. | 2.82 | — | 0.72 | ** | 1.25*** | 0.13 |

*Due to the relatively high viscosity of the carrageenan solution, this formula was prepared utilizing a preheated stearate-glycol dispersion.
**Too viscous for proper dispersion of components (@ >94° C.).
***After thawing, the gel was friable and could be drained of its fluid content with mild pressure.

The excellent physical characteristics of the instant gels were once again exhibited.

Summarizing, it is seen that this invention provides a novel gel composition based on a unique carrageenan-stearate gelling agent. Variations may be made in proportions, procedures and materials without departing from the scope of the invention as defined by the following claims.

What is claimed is:

1. A thermally stable gel composition comprising in an aqueous system from about 1.5-15%, by weight, of carrageenan and a stearate salt selected rom the group consisting of sodium, potassium and alkanolamine stearates, said carrageenan and stearate being present in a weight ratio of 0.3:1 to 5:1; from about 0.5-6.0%, by weight, of a volatile active agent; from about 1 to 20%, by weight, of a component for enhancing stearate solubility selected from the group consisting of glycols and $C_2$-$C_{18}$ alcohols; and water to 100%.

2. A gel composition of claim 1, wherein the weight ratio of carrageenan to stearate is 1:1 to 3:1.

3. The gel composition of claim 1, wherein said stearate is sodium or potassium stearate.

4. The gel composition of claim 1, wherein said solubility component is selected from the group consisting of ethylene glycol, diethylene glycol, triethylene glycol, tetraethylene glycol, propylene glycol, liquid polyethylene glycols, solid polyethylene glycols, ethylene glycol monomethyl ether, polyethylene glycol monomethyl ether, ethanol, butanol, hexanol and cetyl alcohol.

5. The gel composition of claim 4, wherein said solubility component is ethylene glycol, propylene glycol or ethanol.

6. A method for dispensing a volatile active agent over an extended period of time comprising exposing to the atmosphere a gel composition comprising in an aqueous system from about 1.5-15%, by weight, of carrageenan and a stearate salt selected from the group consisting of sodium, potassium and alkanolamine stearates, said carrageenan and stearate being present in a weight ratio of 0.3:1 to 5:1; from about 0.5-6.0% by weight, of a volatile active agent; from about 1 to 20%, by weight, of a component for enhancing stearate solubility selected from the group consisting of glycols and $C_2$-$C_{18}$ alcohols; and water to 100%, and allowing the volatiles in said gel to evaporate.

7. The method of claim 6, wherein the weight ratio of carrageenan to stearate is 1:1 to 3:1.

* * * * *